(12) United States Patent
Rapta et al.

(10) Patent No.: US 8,697,724 B2
(45) Date of Patent: Apr. 15, 2014

(54) CRYSTALLINE OXALATE SALTS OF A DIAMIDE COMPOUND

(75) Inventors: Miroslav Rapta, Sunnyvale, CA (US); Venkat R. Thalladi, Foster City, CA (US); Robert S. Chao, Santa Clara, CA (US)

(73) Assignee: Theravance, Inc., South San Francisco, CA (US)

( * ) Notice: Subject to any disclaimer, the term of this patent is extended or adjusted under 35 U.S.C. 154(b) by 165 days.

(21) Appl. No.: 13/248,840

(22) Filed: Sep. 29, 2011

(65) Prior Publication Data

US 2012/0083478 A1  Apr. 5, 2012

Related U.S. Application Data

(60) Provisional application No. 61/388,148, filed on Sep. 30, 2010.

(51) Int. Cl.
*A61K 31/04* (2006.01)
*C07D 215/38* (2006.01)

(52) U.S. Cl.
USPC .................. 514/312; 514/171; 546/167

(58) Field of Classification Search
USPC .................. 546/167; 514/312, 171
See application file for complete search history.

(56) References Cited

U.S. PATENT DOCUMENTS

| 7,141,671 | B2 | 11/2006 | Mammen et al. |
| 7,320,990 | B2 | 1/2008 | Chao et al. |
| 7,521,558 | B2 | 4/2009 | Chao et al. |
| 7,880,010 | B2 | 2/2011 | Bolton et al. |
| 7,960,551 | B2 | 6/2011 | Chudasama et al. |
| 8,138,345 | B2 * | 3/2012 | Hughes et al. ........... 546/157 |
| 2004/0167167 | A1 | 8/2004 | Mammen et al. |
| 2005/0182092 | A1 | 8/2005 | Chao et al. |
| 2006/0035931 | A1 | 2/2006 | Chao et al. |
| 2007/0249674 | A1 | 10/2007 | Bolton et al. |
| 2007/0281971 | A1 | 12/2007 | Chudasama et al. |
| 2010/0273755 | A1 | 10/2010 | Hughes et al. |

FOREIGN PATENT DOCUMENTS

WO    2010/123766 A1    10/2010

OTHER PUBLICATIONS

Berge et al., "Pharmaceutical Salts", Journal of Pharmaceutical Sciences, 66(1): 1-19 (1977).
International Search Report for PCT/US2011/053997 dated Dec. 27, 2011.
Gould et al., "Salt Selection for Basic Drugs", International Journal of Pharmaceutics, 33: 201-217 (1986).
Laird, "Polymorphism—Still Unpredictable?", Organic Process Research & Development, 14(1): 1 (2010).
Paulekuhn et al., "Trends in Active Pharmaceutical Ingredient Salt Selection Based on Analysis of the Orange Book Database", Journal of Med. Chem, 50: 6665-6672 (2007).

* cited by examiner

*Primary Examiner* — D M Seaman
(74) *Attorney, Agent, or Firm* — Jeffrey A. Hagenah (57) ABSTRACT

The invention relates to crystalline oxalate salts of biphenyl-2-ylcarbamic acid 1-(2-{[4-(4-{[(R)-2-hydroxy-2-(8-hydroxy-2-oxo-1,2-dihydroquinolin-5-yl)ethylamino]-methyl}phenylcarbamoyl)butyl]methylcarbamoyl}ethyl) piperidin-4-yl ester. This invention also relates to compositions containing such a crystalline oxalate salt; methods of using such a crystalline oxalate salt to, for example, treat a pulmonary disorder; and to processes for preparing such a crystalline oxalate salt.

34 Claims, 4 Drawing Sheets

CRYSTALLINE OXALATE SALTS OF A DIAMIDE COMPOUND

CROSS-REFERENCE TO RELATED APPLICATIONS

This application claims the benefit of U.S. Provisional Application No. 61/388,148, filed on Sep. 30, 2010; the entire disclosure of which is incorporated herein by reference in its entirety.

BACKGROUND OF THE INVENTION

1. Field of the Invention

The present invention relates to novel crystalline oxalate salts of a diamide compound. This invention also relates to pharmaceutical compositions containing such crystalline salts; processes and intermediates useful for preparing such crystalline salts; and methods of using such crystalline salts to, for example, treat a pulmonary disorder.

2. State of the Art

U.S. Patent Application Publication No. US 2010/0273755 A1, published on Oct. 28, 2010, discloses diamide compounds that are expected to be useful as therapeutic agents for treating pulmonary disorders, such as chronic obstructive pulmonary disease (COPD) and asthma. One compound disclosed in this application is biphenyl-2-ylcarbamic acid 1-(2-{[4-(4-{[(R)-2-hydroxy-2-(8-hydroxy-2-oxo-1,2-dihydroquinolin-5-yl)ethylamino]-methyl}phenylcarbamoyl)butyl]methylcarbamoyl}-ethyl)piperidin-4-yl ester, which has the chemical structure represented by formula I:

Therapeutic agents used for treating pulmonary disorders are typically administered directly into the respiratory tract using an inhalation device, such as a dry powder inhaler (DPI), a metered-dose inhaler (MDI) or a nebulizer inhaler. When formulating a therapeutic agent for use in such devices, it is advantageous to have a stable crystalline form of the therapeutic agent that can be micronized or otherwise formulated and stored without significant decomposition or loss of crystallinity. In particular, the crystalline form should not be excessively hygroscopic or deliquescent. Additionally, the crystalline form should have a relatively high melting point (i.e. greater than about 130° C.) to minimize thermal degradation during processing and storage.

However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use in, e.g., pharmaceutical inhalation devices.

At present, no crystalline form of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester has been disclosed. Accordingly, a need exists for a stable crystalline form of this compound. In particular, a need exists for a stable, non-deliquescent crystalline form which has an acceptable level of hygroscopicity and a relatively high melting point.

SUMMARY OF THE INVENTION

The present invention relates to oxalic acid addition salts of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}ethyl)piperidin-4-yl ester in crystalline solid state form. Such crystalline oxalate salts include crystalline oxalate isopropanol solvate salts and crystalline oxalate hydrate salts.

Certain crystalline oxalate salts of the invention have been discovered to be non-deliquescent and to have acceptable hygroscopicity properties when exposed to atmospheric moisture. Moreover, the crystalline oxalate salts of the present invention have a relatively high melting point of at least about 160° C.

Accordingly, in one aspect, the present invention provides a crystalline oxalate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester.

In one embodiment, the crystalline oxalate salt of the invention is an isopropanol solvate characterized by a powder x-ray diffraction pattern comprising diffraction peaks at 2θ values of 11.66±0.20, 15.75±0.20, 19.55±0.20, 23.00±0.20 and 23.45±0.20. This crystalline form or polymorph has been designated as Form 1.

In another embodiment, the crystalline oxalate salt of the invention is a hydrate characterized by a powder x-ray diffraction pattern comprising diffraction peaks at 2θ values of 15.32±0.20, 16.90±0.20, 19.25±0.20 and 23.73±0.20. This crystalline form or polymorph has been designated as Form 2.

In one embodiment, the crystalline oxalate salt of the invention is a hydrate prepared by by exposing a crystalline oxalate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester to about 80% to about 100% relative humidity for a period of about 1 to about 5 days.

In another aspect, the present invention provides a composition comprising a crystalline oxalate salt of the invention.

In one embodiment, the composition is a pharmaceutical composition comprising (a) a crystalline oxalate salt of the invention and (b) a pharmaceutically-acceptable carrier.

In another embodiment, the composition is a pharmaceutical composition comprising (a) a crystalline oxalate salt of the invention; (b) a steroidal anti-inflammatory agent or a pharmaceutically acceptable salt or solvate thereof; and (c) a pharmaceutically-acceptable carrier.

In another aspect, the present invention provides a crystalline oxalate salt of the invention for use in therapy.

In one embodiment, a crystalline oxalate salt of the invention is used in the treatment of a pulmonary disorder. In a particular embodiment, the pulmonary disorder is chronic obstructive pulmonary disease. In another particular embodiment, the pulmonary disorder is asthma.

In one embodiment, the present invention provides a method of treating a pulmonary disorder, the method comprising administering to a patient a crystalline oxalate salt of the invention.

In another embodiment, the present invention provides a method of treating a pulmonary disorder, the method comprising administering to a patient (a) a crystalline oxalate salt of the invention; and (b) a steroidal anti-inflammatory agent or a pharmaceutically acceptable salt or solvate thereof.

In yet another embodiment, the present invention provides a method of producing bronchodilation in a mammal, the method comprising administering a crystalline oxalate salt of the invention to the mammal by inhalation.

In another embodiment, the present invention provides a crystalline oxalate salt of the invention for use in the manufacture of a medicament.

Other aspects and embodiments of this invention are disclosed herein.

BRIEF DESCRIPTION OF THE DRAWINGS

Various aspects of the present invention are illustrated by reference to the accompanying drawings.

DETAILED DESCRIPTION OF THE INVENTION

This present invention relates to oxalic acid addition salts of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}ethyl)piperidin-4-yl ester in crystalline solid state form including isopropanol solvates and hydrates thereof. The crystalline oxalate salts of the invention may be present as one or more distinct crystalline solid state forms and the present invention encompasses all such forms, including mixtures of forms, unless otherwise indicated.

In one embodiment, the present invention provides a first crystalline oxalate solid state form of the oxalic acid addition salt of the compound of formula I referred to herein as Form 1. Form 1 is an isopropanol solvate form.

In another embodiment, the present invention provides a second crystalline oxalate solid state form of the oxalic acid addition salt of the compound of formula I referred to herein as Form 2. Form 2 is a hydrate.

The compound of formula I contains one chiral center having the (R) configuration. However, it will be understood by those skilled in the art that minor amounts of the (S) stereoisomer may be present in the compositions of this invention unless otherwise indicated, provided that any utility of the composition as a whole is not eliminated by the presence of such an isomer.

The compound of formula I and intermediates thereof have been named using the AutoNom feature of the commercially-available MDL® ISIS/Draw software (Symyx, Santa Clara, Calif.).

DEFINITIONS

When describing the compounds, compositions, methods and processes of this invention, the following terms have the following meanings unless otherwise indicated.

The term "melting point" means the temperature at which the maximum endothermic heat flow is observed by differential scanning calorimetry.

The term "micronized" or "in micronized form" means particles in which at least about 90 percent of the particles have a diameter of less than about 10 μm.

The term "solvate" means an association, such as a complex or an aggregate, of one or more molecules of a solute, i.e. an oxalate salt of the compound of formula I, and one or more molecules of a solvent. Representative solvents include, by way of example, water and isopropanol. When the solvent is water, the solvate formed is a hydrate.

The term "therapeutically effective amount" means an amount sufficient to effect treatment when administered to a patient in need of treatment.

The term "treating" or "treatment" means:
(a) ameliorating a disease or medical condition, i.e., eliminating or causing regression of the disease or medical condition in a patient;
(b) suppressing a disease or medical condition, i.e., slowing or arresting the development of the disease or medical condition in a patient; or
(c) alleviating the symptoms of a disease or medical condition in a patient.

The term "unit dosage form" means a physically discrete unit suitable for dosing a patient, i.e., each unit containing a predetermined quantity of a therapeutic agent calculated to produce a therapeutic effect either alone or in combination with one or more additional units. For example, such unit dosage forms may be dry powder inhaler capsules, a metered dose from a metered dose inhaler, capsules, tablets, pills, and the like.

Representative Crystalline Oxalate Salts of the Invention

Crystalline oxalate salts of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester have been discovered to exist in at least two different crystalline forms. For purposes of this invention, these forms are identified herein as Form 1 and Form 2.

Form 1 is an isopropanol solvate characterized by a powder x-ray diffraction (PXRD) pattern having significant diffraction peaks, among other peaks, at 2θ values of about 11.66±0.20, 15.75±0.20, 19.55±0.20, 23.00±0.20 and 23.45±0.20. Form 1 has a differential scanning calorimetry (DSC) trace that exhibits a peak in endothermic heat flow at about 162° C. to about 164° C., e.g., at about 163.3° C. Form 1 comprises about 1 to about 2 molar equivalents of isopropanol per molar equivalent of oxalate salt of the compound of formula I, including about 1.25 to about 1.75 molar equivalents, such as 1.5 molar equivalents.

Form 2 is a hydrate characterized by a powder x-ray diffraction (PXRD) pattern having significant diffraction peaks, among other peaks, at 2θ values of about of 15.32±0.20, 16.90±0.20, 19.25±0.20 and 23.73±0.20. Form 2 has a differential scanning calorimetry (DSC) trace that exhibits a peak in endothermic heat flow at about 162° C. to about 164° C., e.g., at about 162.6° C. Form 2 comprises about 1 to about 3 molar equivalents of water per molar equivalent of oxalate salt of the compound of formula I, including about 1.5 to about 2 molar equivalents.

The crystalline oxalate salts of this invention typically contains between about 0.90 and about 1.10 molar equivalents of oxalic acid per molar equivalent of the compound of formula I; including between about 0.95 and about 1.05 molar equivalents of oxalic acid per molar equivalent of the compound of formula I. In a particular embodiment, the oxalic acid salt of this invention contains about 1 molar equivalent of oxalic acid per molar equivalent of the compound of formula I. The molar ratio is determined using conventional methods, such as $^{13}C$ NMR, elemental analysis, ion analysis or HPLC.

The crystalline oxalate salts of this invention are typically prepared using oxalic acid or oxalic acid dihydrate and biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester. Oxalic acid and oxalic acid dihydrate are commercially-available, e.g., from Sigma-Aldrich, St. Louis, Mo. The biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester employed in this invention can be readily prepared from commercially-available starting materials and reagents using the procedures described in the Examples below; or by using the procedures described in the commonly-assigned U.S. application described in the Background section of this application.

Methods or processes for preparing crystalline oxalate salts of this invention are provided in the Examples. Typically, biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester is contacted with about 0.90 to about 1.1 molar equivalents, such as 1.0 molar equivalents, of oxalic acid or oxalic acid dihydrate in a diluent. Generally, this reaction is conducted at a temperature ranging from about 0 EC to about 60 EC; including about 20 EC to about 35 EC, such as about 25 EC to about 30 EC. Suitable inert diluents for this reaction include, but are not limited to, methanol, isopropanol, and the like optionally containing water. Optionally, the reaction mixture can be sonicated using conventional equipment to facilitate crystallization.

A process of preparing a crystalline oxalate salt of this invention can optionally include the use of a seed crystal to produce predominately a particular crystalline form. For example, by using a seed crystal of Form 2, a crystalline oxalate hydrate salt can be prepared having essentially the same form as the seed crystal, i.e. Form 2. Such seed crystals can be used when initially forming the crystalline oxalate salt of the invention or they can be used to recrystallize a crystalline or partially crystalline form.

Typically, seed crystals are prepared by slow crystallization without stirring and without applying cooling. By way of illustration, to obtain seed crystals, the compound of formula I is typically dissolved in a diluent at a temperature sufficient to provide dissolution. For example, the compound of formula I is dissolved in hot 10% (v/v) water in methanol and then allowed to cool to ambient temperature. This solution is allowed evaporate slowly to provide a crystalline oxalate salt of the invention. The resulting crystals are isolated by filtration or other conventional means. Alternatively, seed crystals may be obtain from a previous preparation of crystalline material.

The crystallinity of Form 2 has been found to improve when the crystalline material is stored at ambient temperature under high humidity. For example, when a sample of Form 2 was stored at ambient temperature at 84% relative humidity, the crystallinity improved over a period of about 5 days as measured by the PXRD pattern of the sample.

Compositions, Combinations and Formulations

The crystalline oxalate salts of this invention may be combined with other materials, such as therapeutic agents, carriers, excipients, diluents, solvents, and the like, to form compositions.

In one embodiment, a crystalline oxalate salt of the invention is formulated with a carrier or excipient to form a pharmaceutical composition or formulation. Such pharmaceutical compositions will typically contain a therapeutically effective amount of a crystalline oxalate salt of the invention. In some cases, however, the pharmaceutical composition may contain more than a therapeutically effective amount, e.g., a concentrated bulk composition; or less than a therapeutically effective amount, e.g., a unit dosage form intended for multiple unit administration.

The pharmaceutical composition will typically contain from about 0.01 to about 95 percent by weight of a crystalline oxalate salt of the invention including, for example, from about 0.05 to about 30 percent by weight; or from about 0.1 to about 10 percent by weight.

Such pharmaceutical compositions can be prepared using conventional carriers or excipients. The choice of a particular carrier or excipient, or combinations of carriers or excipients, will depend on various factors such as the mode of administration, or the disease or medical condition being treated. Many suitable carriers and excipients for preparing pharmaceutical compositions are commercially available. For example, materials can be purchased from Sigma (St. Louis, Mo.). Procedures and materials for preparing pharmaceutical compositions suitable for a particular mode of administration are described in the pharmaceutical arts including, for example, *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of pharmaceutically-acceptable carriers include, but are not limited to: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) solidified oils and waxes, such as cocoa butter and suppository waxes; (9) liquid oils (at room temperature), such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) compressed propellant gases, such as chlorofluorocarbons and hydrofluorocarbons; and (22) other non-toxic compatible substances employed in pharmaceutical compositions.

The pharmaceutical composition is typically prepared by thoroughly and intimately mixing or blending a crystalline oxalate salt of the invention with a pharmaceutically-acceptable carrier and any other optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical composition is suitable for inhaled administration. Pharmaceutical compositions for inhaled administration are typically in the form of an aerosol or a powder. Such compositions are generally administered using inhaler delivery devices, such as a metered-dose inhaler (MDI), a dry powder inhaler (DPI), a nebulizer inhaler, or a similar delivery device.

In a particular embodiment, the pharmaceutical composition is administered by inhalation using a dry powder inhaler. Such dry powder inhalers typically administer the pharmaceutical composition as a free-flowing powder that is dispersed in a patient's air-stream during inspiration. In order to achieve a free-flowing powder composition, the therapeutic agent is typically formulated with a suitable excipient such as lactose, starch, mannitol, dextrose, polylactic acid (PLA), polylactide-co-glycolide (PLGA) or combinations thereof. Typically, the therapeutic agent is micronized and combined with a suitable carrier to form a composition suitable for inhalation. Accordingly, in one embodiment, the crystalline oxalate salt of the invention is in micronized form.

A representative pharmaceutical composition for use in a dry powder inhaler comprises lactose and a crystalline oxalate salt of the invention in micronized form. Such a dry powder composition can be made, for example, by combining dry milled lactose with the therapeutic agent and then dry blending the components. The composition is then typically loaded into a dry powder dispenser, or into inhalation cartridges or capsules for use with a dry powder delivery device.

Dry powder inhaler delivery devices suitable for administering therapeutic agents by inhalation are described in the art and examples of such devices are commercially available. For example, representative dry powder inhaler delivery devices or products include Aeolizer (Novartis); Airmax (IVAX); ClickHaler (Innovata Biomed); Diskhaler (GlaxoSmithKline); Diskus/Accuhaler (GlaxoSmithKline); Easyhaler (Orion Pharma); Eclipse (Aventis); FlowCaps (Hovione); Handihaler (Boehringer Ingelheim); Pulvinal (Chiesi); Rotahaler (GlaxoSmithKline); SkyeHaler/Certihaler (SkyePharma); Twisthaler (Schering-Plough); Turbuhaler (AstraZeneca); Ultrahaler (Aventis); and the like.

In another particular embodiment, the pharmaceutical composition is administered by inhalation using a metered-dose inhaler. Such metered-dose inhalers typically discharge a measured amount of a therapeutic agent using a compressed propellant gas. Accordingly, pharmaceutical compositions administered using a metered-dose inhaler typically comprise a solution or suspension of the therapeutic agent in a liquefied propellant. Any suitable liquefied propellant may be employed including hydrofluoroalkanes (HFAs), such as 1,1,1,2-tetrafluoroethane (HFA 134a) and 1,1,1,2,3,3,3-heptafluoro-n-propane, (HFA 227); and chlorofluorocarbons, such as $CCl_3F$. In a particular embodiment, the propellant is hydrofluoroalkanes. In some embodiments, the hydrofluoroalkane formulation contains a co-solvent, such as ethanol or pentane, and/or a surfactant, such as sorbitan trioleate, oleic acid, lecithin, and glycerin.

A representative pharmaceutical composition for use in a metered-dose inhaler comprises from about 0.01% to about 5% by weight of a crystalline oxalate salt of the invention; from about 0% to about 20% by weight ethanol; and from about 0% to about 5% by weight surfactant; with the remainder being an HFA propellant. Such compositions are typically prepared by adding chilled or pressurized hydrofluoroalkane to a suitable container containing the therapeutic agent, ethanol (if present) and the surfactant (if present). To prepare a suspension, the therapeutic agent is micronized and then combined with the propellant. The composition is then loaded into an aerosol canister, which typically forms a portion of a metered-dose inhaler device.

Metered-dose inhaler devices suitable for administering therapeutic agents by inhalation are described in the art and examples of such devices are commercially available. For example, representative metered-dose inhaler devices or products include AeroBid Inhaler System (Forest Pharmaceuticals); Atrovent Inhalation Aerosol (Boehringer Ingelheim); Flovent (GlaxoSmithKline); Maxair Inhaler (3M); Proventil Inhaler (Schering); Serevent Inhalation Aerosol (GlaxoSmithKline); and the like.

In another particular embodiment, the pharmaceutical composition is administered by inhalation using a nebulizer inhaler. Such nebulizer devices typically produce a stream of high velocity air that causes the pharmaceutical composition to spray as a mist that is carried into the patient's respiratory tract. Accordingly, when formulated for use in a nebulizer inhaler, the therapeutic agent can be dissolved in a suitable carrier to form a solution. Alternatively, the therapeutic agent can be micronized and combined with a suitable carrier to form a suspension of micronized particles.

A representative pharmaceutical composition for use in a nebulizer inhaler comprises an isotonic aqueous suspension comprising from about 0.05 μg/mL to about 10 mg/mL of a crystalline oxalate salt of the invention in micronized form. In one embodiment, the solution has a pH of about 4 to about 6.

Nebulizer devices suitable for administering therapeutic agents by inhalation are described in the art and examples of such devices are commercially available. For example, representative nebulizer devices or products include the Respimat Softmist Inhalaler (Boehringer Ingelheim); the AERx Pulmonary Delivery System (Aradigm Corp.); the PARI LC Plus Reusable Nebulizer (Pari GmbH); and the like.

If desired, a crystalline oxalate salt of the invention may be administered in combination with one or more other therapeutic agents. In this aspect of the invention, a crystalline oxalate salt of the invention is either physically mixed with the other therapeutic agent to form a composition containing both agents; or each agent is administered separately to the patient either simultaneously or sequentially.

For example, a crystalline oxalate salt of the invention can be combined with second therapeutic agent using conventional procedures and equipment to form a composition comprising the crystalline oxalate salt of the invention and the second therapeutic agent. Additionally, the therapeutic agents may be combined with a pharmaceutically-acceptable carrier to form a pharmaceutical composition comprising a crystalline oxalate salt of the invention, a second therapeutic agent and a pharmaceutically-acceptable carrier. In this embodiment, the components of the composition are typically mixed or blended to create a physical mixture. The physical mixture is then administered to a patient using any of the routes described herein.

Alternatively, the therapeutic agents may remain separate and distinct before administration to the patient. In this embodiment, the therapeutic agents are not physically mixed together before administration but are administered simultaneously or sequentially as separate agents or compositions. For example, a crystalline oxalate salt of the invention can be administered by inhalation simultaneously or sequentially with another therapeutic agent using an inhalation delivery device that employs separate compartments (e.g. blister packs) for each therapeutic agent. Alternatively, the combination may be administered using separate delivery devices, i.e., one delivery device for each therapeutic agent. Additionally, the therapeutic agents can be delivered by different routes of administration, i.e., one by inhalation and the other by oral administration.

Any therapeutic agent compatible with crystalline oxalate salt of the invention may be used in combination with such salts. In a particular embodiment, the second therapeutic agent is one that is effectively administered by inhalation. By way of illustration, representative types of therapeutic agents that may be used include, but are not limited to, anti-inflammatory agents, such as steroidal anti-inflammatory agents (including corticosteroids and glucocorticoids), non-steroidal anti-inflammatory agents (NSAIDs), and $PDE_4$ inhibitors; bronchodilators, such as $PDE_3$ inhibitors, adenosine 2b modulators and β2 adrenergic receptor agonists; anti-infective agents, such as Gram-positive antibiotics, Gram-negative antibiotics, and antiviral agents; antihistamines; protease inhibitors; afferent blockers, such as $D_2$ agonists and neurokinin modulators; and muscarinic receptor antagonists (antichlolinergic agents). Numerous examples of such therapeutic agents are known in the art. Suitable doses for these other therapeutic agents are also known in the art and typically range from about 0.05 μg/day to about 500 mg/day. In one embodiment, the second therapeutic agent is useful for treating a pulmonary disorder.

In a particular embodiment, a crystalline oxalate salt of the invention is administered in combination with a steroidal anti-inflammatory agent. Representative steroidal anti-inflammatory agents include, but are not limited to, beclomethasone dipropionate; budesonide; butixocort propionate; 20R-16α,17α-[butylidenebis(oxy)]-6α,9α-difluoro-11β-hydroxy-17β-(methylthio)androsta-4-en-3-one (RPR-106541); ciclesonide; dexamethasone; 6α,9α-difluoro-17α-[(2-furanylcarbonyl)oxy]-11β-hydroxy-16α-methyl-3-oxoandrosta-1,4-diene-17β-carbothioic acid S-fluoromethyl ester; 6α,9α-difluoro-11β-hydroxy-16α-methyl-17α-[(4-methytl-1,3-thiazole-5-carbonyl)oxy]-3-oxoandrosta-1,4-diene-17β-carbothioic acid S-fluoromethyl ester; 6α,9α-difluoro-11β-hydroxy-16α-methyl-3-oxo-17α-propionyloxyandrosta-1,4-diene-17β-carbothioic acid (S)-(2-oxotetrahydrofuran-3S-yl) ester; flunisolide; fluticasone furoate; fluticasone propionate; methyl prednisolone; mometasone furoate; prednisolone; prednisone; rofleponide; ST-126; triamcinolone acetonide; and the like, and pharmaceutically acceptable salts and solvates thereof. Such steroidal anti-inflammatory agents are commercially available or can be prepared using conventional procedures and reagents. For example, the preparation and use of steroidal anti-inflammatory agents is described in U.S. Pat. No. 6,537,983, issued Mar. 25, 2003; U.S. Pat. No. 6,750,210 B2, issued Jun. 15, 2004; U.S. Pat. No. 6,759,398 B2, issued Jul. 6, 2004; U.S. Pat. No. 6,858,596 B2, issued Feb. 22, 2005; U.S. Pat. No. 7,101,866 B2, issued Sep. 5, 2006; and the references cited therein.

When employed, the steroidal anti-inflammatory agent is typically administered in an amount that produces a therapeutically beneficial effect when co-administered with a crystalline oxalate salt of the invention. Typically, the steroidal anti-inflammatory agent will be administered in an amount sufficient to provide from about 0.05 μg to about 500 μg of the agent per dose.

Representative pharmaceutical compositions include, but are not limited, to the following examples:

A. Dry Powder Composition

A micronized crystalline oxalate salt of the invention (100 mg) is blended with dry milled lactose (25 g). This blended mixture is then loaded into individual blisters of a peelable blister pack in an amount sufficient to provide about 10 μg to about 500 μg of a crystalline oxalate salt of the invention per dose. The contents of the blisters are administered using a dry powder inhaler.

B. Dry Powder Composition

A micronized crystalline oxalate salt of the invention (1 g) is blended with dry milled lactose (200 g) to form a bulk composition having a weight ratio of crystalline oxalate salt to lactose of 1:200. The blended composition is packed into a dry powder inhalation device capable of delivering between about 10 μg to about 500 μg of a crystalline oxalate salt of the invention per dose.

C. Dry Powder Composition

A micronized crystalline oxalate salt of the invention (100 mg) and a micronized steroidal anti-inflammatory agent (500 mg) are blended with dry milled lactose (30 g). This blended mixture is then loaded into individual blisters of a peelable blister pack in an amount sufficient to provide about 10 μg to about 500 μg of a crystalline oxalate salt of the invention per dose. The contents of the blisters are administered using a dry powder inhaler.

D. Metered-Dose Inhaler Composition A micronized crystalline oxalate salt of the invention (10 g) is dispersed in a solution prepared by dissolving lecithin (0.2 g) in demineralized water (200 mL). The resulting suspension is spray dried and then micronized to form a micronized composition comprising particles having a mean diameter less than about 1.5 μm. The micronized composition is then loaded into metered-dose inhaler cartridges containing pressurized 1,1,1,2-tetrafluoroethane in an amount sufficient to provide about 10 μg to about 500 μg of a crystalline oxalate salt of the invention per dose when administered by the metered dose inhaler.

Utility

Biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester possesses both $\beta_2$ adrenergic receptor agonist and muscarinic receptor antagonist activity and therefore, an oxalate salt of this compound is expected to be useful as a therapeutic agent for treating medical conditions mediated by $\beta_2$ adrenergic receptors or muscarinic receptors, i.e., medical conditions that are ameliorated by treatment with a $\beta_2$ adrenergic receptor agonist or a muscarinic receptor antagonist.

Such medical conditions are known in the art as exemplified by, for example, the teachings of Eglen et al., *Muscarinic Receptor Subtypes: Pharmacology and Therapuetic Potential, DN&P* 10(8), 462-469 (1997); Emilien et al., *Current Therapeutic Uses and Potential of beta-Adrenoceptor Agonists and Antagonists, European J. Clinical Pharm.*, 53(6), 389-404 (1998); and references cited therein. For example, such medical conditions include, by way of illustration, pulmonary disorders or diseases associated with reversible airway obstruction, such as chronic obstructive pulmonary disease, asthma, bronchitis, emphysema, pulmonary fibrosis and the like. Chronic obstructive pulmonary disease or COPD is known in the art to include a variety of respiratory conditions, including chronic obstructive bronchitis and emphysema, as exemplified by the teachings of Barnes, *Chronic Obstructive Pulmonary Disease, N Engl. J. Med.*, 2000: 343:269-78, and references cited therein. Other conditions include premature labor, depression, congestive heart failure, skin diseases (e.g., inflammatory, allergic, psoriatic and proliferative skin diseases), conditions where lowering peptic acidity is desirable (e.g., peptic and gastric ulceration) and muscle wasting disease.

In one aspect, this invention provides a crystalline oxalate salt of the invention for use in therapy. For example, a crystalline oxalate salt of the invention can be used to treat a pulmonary disorder, such as chronic obstructive pulmonary disease or asthma.

When used to treat a pulmonary disorder, the crystalline oxalate salt of this invention is administered to a patient in need of treatment. In one embodiment, the crystalline oxalate salt is administered by inhalation. The crystalline oxalate salt of the invention can be administered in multiple doses per day (e.g., b.i.d. or t.i.d.), in one dose per day (e.g., q.d.), in a single dose per week, or as needed. Generally, the dose for treating a pulmonary disorder will range from about 10 μg/day to about 1,000 μg/day.

When administered to a mammal by inhalation, the crystalline oxalate salts of this invention typically produce bronchodilation and therefore, the crystalline oxalate salts of this invention are useful as agents for producing bronchodilation in a mammal, such as a human, dog, guinea pig, rat and the like. In this embodiment, the crystalline oxalate salt of the invention is typically administered by inhalation to the mammal in a bronchodilation-producing amount. Generally, the dose for producing bronchodilation will range from about 0.25 μg/kg to about 20 μg/kg.

When used as a therapeutic agent, the crystalline oxalate salts of this invention are optionally administered in combination with one or more other therapeutic agents. In particular, by administering a crystalline oxalate salt of this invention with a steroidal anti-inflammatory agent, triple pulmonary therapy, i.e., $\beta_2$ adrenergic receptor agonist activity, muscarinic receptor antagonist activity and anti-inflammatory activity, can be achieved using only two therapeutic agents. Since pharmaceutical compositions (and combinations) containing two therapeutic agents are typically easier to formulate and/or administer compared to compositions containing three therapeutic agents, such two component compositions provide a significant advantage over compositions containing three therapeutic agents. Accordingly, in a particular embodiment, the pharmaceutical compositions, combinations and methods of this invention further comprise a steroidal anti-inflammatory agent or a pharmaceutically acceptable salt or solvate thereof.

The properties and utility of the crystalline oxalate salts of this invention can be demonstrated using various in vitro and in vivo assays known to those skilled in the art. For example, representative assays are described in the following Examples.

EXAMPLES

The following examples are provided to illustrate various representative embodiments and aspects of this invention and are not intended to limit the scope of this invention in any way unless specifically indicated.

All reagents, starting materials and solvents used in the following examples were purchased from commercial suppliers (such as Sigma-Aldrich Chemical Company, St. Louis, Mo.) and were used without further purification unless otherwise indicated. The following abbreviations are used for diluents: DCM=dichloromethane; DMF=N,N-dimethylformamide; DMSO=dimethyl sulfoxide; EtOAc=ethyl acetate; MeOH=methanol; and THF=tetrahydrofuran.

$^1$H NMR spectra were recorded on a 400 MHz Varian AS400 spectrometer, unless otherwise indicated. Chemical shifts are reported as δ values in ppm relative to tetramethylsilane (TMS) as an internal standard. Coupling constants (J values) are given in hertz (Hz) and multiplicities are reported using the following abbreviations: s=singlet, d=doublet, t=triplet, q=quartet, m=multiplet, br=broad, nd=not determined.

Liquid Chromatography Mass Spectroscopy (LC-MS) Conditions

LC-MS data were obtained using an Agilent 1100 Liquid Chromatography System—G1312A Binary Pump (Agilent Technologies), a ZORBAX Rapid Resolution 3.5 μm Rx, Bonus-RP column (3.5 μm particle size; 2.1 mm×50 mm) (Agilent Technologies) and API 150EX Single Quadrupole LC/MS Mass Spectrometer (Perkin-Elmer Sciex Instruments). The solvent systems used were:

| | |
|---|---|
| Solvent A: | 98% water and 2% acetonitrile (v/v) + 1 mL/L TFA |
| Solvent B: | 90% acetonitrile and 10% water (v/v) + 1 mL/L TFA |
| Flow Rate: | 500 μL/min |
| Gradient: | (Method 10-90): 10% B to 90% B over 3 min |
| | (Method 2-90): 2% B to 90% B over 3 min |
| | (Method 10-70): 10% B to 70% B over 3 min. |

HPLC Conditions

HPLC was conducted using an HP 1100 Series HPLC System (Agilent Technologies) and a ZORBAX Rapid Resolution 3.5 µm Rx, Bonus-RP column (3.5 µm particle size; 2.1 mm×50 mm) (Agilent Technologies) or an Ascentis Express C18 HPLC column (2.7 µm particle size, 3.0 mm×3 cm). The solvent systems used were:

| | |
|---|---|
| Solvent A: | 98% water and 2% acetonitrile (v/v) + 1 mL/L TFA |
| Solvent B: | 90% acetonitrile and 10% water (v/v) + 1 mL/L TFA |
| Flow Rate: | 500 µL/min |
| Gradient: | (Method 10-50): 10% B to 50% B over 6 min |
| | (Method 10-70): 10% B to 70% B over 6 min |
| | (Method 2-90): 2% B to 90% B over 6 min. |

Example 1

Preparation of 3-[4-(Biphenyl-2-ylcarbamoyloxy) piperidin-1-yl]propionic Acid

A stirred solution of biphenyl-2-ylcarbamic acid piperidin-4-yl ester (50.0 g, 168.7 mmol) (see, e.g., U.S. Patent Publication No. 2006/0035931 A1, published Feb. 16, 2006) and acrylic acid (15.1 mL, 219.3 mmol) in DCM (500 mL) was heated at 50° C. overnight. The reaction mixture was concentrated under reduced pressure and the residue was dissolved in MeOH (600 mL). The resulting solution was heated at 75° C. for 2 h and then allowed to stand at room temperature for about 48 h. The resulting solid was collected by filtration, washed with MeOH, and dried to give the title compound (61.5 g, 99% yield).

Example 2

Preparation of Methyl 5-Methylaminopentanoate Hydrochloride

A stirred solution of 1-methyl-2-piperidinone (4.40 mL, 40.0 mmol) in aqueous sodium hydroxide (4 M, 11.0 mL, 44.0 mmol) was heated at 100° C. for 15 h. The reaction mixture was cooled to room temperature and then acidified to pH 2 with concentrated hydrochloric acid. The mixture was then concentrated under reduced pressure to give crude 5-methylaminopentanoic acid as a pinkish white solid. To the crude 5-methylaminopentanoic acid was added MeOH (40.0 mL, 987 mmol) and concentrated hydrochloric acid (0.33 mL, 4.0 mmol). The resulting cloudy solution was heated at 60° C. for 39 h at which time LC-MS showed remaining starting material. Additional concentrated hydrochloric acid (0.33 mL, 4.0 mmol) was added and the resulting mixture was heated at 60° C. for 33 h and then at 65° C. for an additional 24 h. LC-MS showed remaining starting material. The reaction mixture was concentrated under reduced pressure and a solution of hydrogen chloride in MeOH (1.25 M) was added to the residue. The resulting mixture was heated at 60° C. for 72 h at which time no remaining starting material was observed by LC-MS. The reaction mixture was partially concentrated under reduced pressure and the solid material that formed was removed by filtration, washing with MeOH. The filtrate was then concentrated under reduced pressure to provide methyl 5-methylaminopentanoate hydrochloride (7.57 g, 100% yield) as a light yellow solid.

LC-MS (Method 2-90): Rt 1.10 min; m/z 146.4 [M+H]$^+$.
$^1$H NMR (CD$_3$OD) δ 4.86 (s), 3.66 (s), 3.30 (t), 3.00 (t), 2.69 (s), 2.41 (t), 1.71 (m).

Example 3

Preparation of 5-({3-[4-(Biphenyl-2-ylcarbamoyloxy)piperidin-1-yl]propionyl}methylamino)pentanoic Acid Methyl Ester A mixture of methyl 5-methylaminopentanoate hydrochloride (7.27 g, 40.0 mmol), 3-[4-(biphenyl-2-ylcarbamoyloxy)piperidin-1-yl]propionic acid (13.3 g, 36.0 mmol) and 1-hydroxy-7-azabenzotriazole (5.14 g, 37.8 mmol) in DCM (160 mL) and 2,6-lutidine (12.5 mL, 108 mmol) was stirred at room temperature for 3 h. N-(3-Dimethylaminopropyl)-N-ethylcarbodiimide hydrochloride (10.4 g, 54.0 mmol) was added and the resulting mixture was stirred at room temperature for 2 h. A saturated aqueous sodium bicarbonate solution (~100 mL) was added and the layers were separated. The aqueous layer was extracted with DCM (50 mL) and the organic layers were combined, dried over sodium sulfate, filtered and concentrated under reduced pressure. The residue was purified by silica gel flash chromatography (30-100% EtOAc in hexanes; then 2-10% MeOH in DCM) to give the title compound (12.38 g, 69% yield) as a light yellow thick oil/white solid.

LC-MS (Method 2-90): Rt 2.43 min; m/z 496.6 [M+H]$^+$.
$^1$H NMR (CDCl$_3$) δ 8.10 (d, 1H), 7.40 (m, 6H), 7.20 (m, 2H), 6.58 (s, 1H), 4.74 (m, 1H), 3.66 (d, 3H), 3.37 (t, 1H), 3.29 (m, 1H), 2.97 (s, 2H), 2.91 (s, 1H), 2.70 (m, 4H), 2.49 (m, 2H), 2.34 (m, 4H), 1.92 (m, 2H), 1.60 (m, 5H).

Example 4

Preparation of 5-({3-[4-(Biphenyl-2-ylcarbamoyloxy)piperidin-1-yl]propionyl}methylamino)pentanoic Acid To a mixture of 5-({3-[4-(biphenyl-2-ylcarbamoyloxy)piperidin-1-yl]propionyl}-methylamino)pentanoic acid methyl ester (10.21 g, 20.60 mmol), tert-butyl alcohol (20 mL) and water (20 mL) was added a 1:1 mixture of LiOH:water (1.97 g, 41.2 mmol). The resulting mixture was stirred at room temperature for 4 h and then the pH of the mixture was adjusted to about pH 2 using aqueous hydrochloric acid (1 N). The aqueous layer was extracted with DCM (2×~80 mL) and the organic layers were combined, dried over sodium sulfate, filtered, and concentrated under reduced pressure to give the title compound (12.23 g, quantitative) as an off-white foamy solid (containing residual tert-butyl alcohol).

LC-MS (Method 2-90): Rt 2.32 min; m/z 482.4 [M+H]$^+$.

Example 5

Preparation of 2-(4-Nitrophenyl)-1,3-dioxolane

A stirred solution of p-nitrobenzaldehyde (101.5 g, 672 mmol), ethylene glycol (112 mL) and p-toluenesulfonic acid (12.8 g, 67.2 mmol) in toluene (800 mL) was heated in flask equipped with a Dean-Stark trap at 120° C. for 4 h. After cooling to room temperature, the reaction mixture was concentrated under reduced pressure. To the residue was added saturated aqueous sodium bicarbonate (800 mL) and this mixture was stirred at room temperature for 15 min. The resulting solid was isolated by filtration and dried under vacuum to give the title compound (121.8 g, 92% yield) as a yellow solid.

$^1$H NMR (DMSO-d$_6$): δ=8.12 (d, 2H), 7.59 (d, 2H), 5.78 (s, 1H), 3.8-4.0 (m, 4H).

Example 6

Preparation of 4-(1,3-Dioxolan-2-yl)phenylamine

To a mixture of platinum dioxide (227 mg, 1.00 mmol) and sodium bicarbonate (420 mg, 5.00 mmol) under dry nitrogen was added a solution of 2-(4-nitrophenyl)-1,3-dioxolane (976 mg, 5.00 mmol) in EtOH (30.0 mL). The reaction mixture was bubbled with hydrogen for 15 min and then stirred under a hydrogen atmosphere (balloon) for 2 h. The reaction mixture was then filtered through a pad of Celite washing with MeOH. The filtrate was concentrated under reduced pressure to give the title compound (0.80 g, 96% yield).

Example 7

Preparation of Biphenyl-2-ylcarbamic Acid 1-(2-{[4-(4-(1,3-Dioxolan-2-yl)-phenylcarbamoyl)butyl]methylcarbamoyl}ethyl)piperidin-4-yl Ester To a stirred solution of 5-({3-[4-(biphenyl-2-ylcarbamoyloxy)piperidin-1-yl]-propionyl}methylamino)pentanoic acid (2.33 g, 4.84 mmol), 4-(1,3-dioxolan-2-yl)phenylamine (800 mg, 5 mmol) and N,N-diisopropylethylamine (1.26 mL, 7.26 mmol) in DCM (48.4 mL) was added 1-hydroxy-7-azabenzotriazole (692 mg, 5.08 mmol) and N-(3-dimethylaminopropyl)-N'-ethylcarbodiimide hydrochloride (1.39 g, 7.26 mmol). The resulting mixture was stirred at room temperature overnight. The reaction mixture was then washed with saturated aqueous sodium bicarbonate solution, dried over sodium sulfate, filtered and concentrated under reduced pressure to give the title compound (3.04 g, 100% yield) as a yellow solid.

LC-MS (Method 10-70): Rt 2.67 min; m/z 629.6 [M+H]$^+$.

Example 8

Preparation of Biphenyl-2-ylcarbamic Acid 1-(2-{[4-(4-Formylphenylcarbamoyl)butyl]methylcarbamoyl}ethyl)piperidin-4-yl Ester A stirred mixture of biphenyl-2-ylcarbamic acid 1-(2-{[4-(4-(1,3-dioxolan-2-yl)phenylcarbamoyl)butyl]methylcarbamoyl}ethyl)piperidin-4-yl ester (3.04 g, 4.84 mmol) in aqueous hydrochloric acid (1 M, 10 mL) and acetonitrile (10 mL) was heated at 50° C. for 2 h. The reaction mixture was concentrated under reduced pressure and saturated aqueous sodium bicarbonate solution and DCM were added to the residue. The layers were separated and the organic layer was dried over sodium sulfate, filtered and concentrated under reduced pressure to give the title compound (2.83 g, 100% yield).

LC-MS (Method 10-70): Rt 2.67 min; m/z 585.4 [M+H]$^+$.

Example 9

Preparation of Biphenyl-2-ylcarbamic Acid 1-(2-{[4-(4-{[(R)-2-(tert-butyldimethyl-silanyloxy)-2-(8-hydroxy-2-oxo-1,2-dihydroquinolin-5-yl)ethylamino]methyl}-phenylcarbamoyl)butyl]methylcarbamoyl}ethyl)piperidin-4-yl Ester To a stirred solution of biphenyl-2-ylcarbamic acid 1-(2-{[4-(4-formyl-phenylcarbamoyl)butyl]methylcarbamoyl}ethyl)piperidin-4-yl ester (2.83 g, 4.84 mmol) and 5-[(R)-2-amino-1-(tert-butyldimethylsilanyloxy)ethyl]-8-hydroxy-1H-quinolin-2-one acetic acid salt (1.91 g, 4.84 mmol) in a 1:1 mixture of MeOH:DCM (40.0 mL, 312 mmol) was added sodium triacetoxyborohydride (3.08 g, 14.5 mmol). The reaction mixture was stirred at room temperature for 2 h and then the layers were separated. The organic layer was washed with saturated aqueous sodium bicarbonate solution, dried over sodium sulfate, filtered and concentrated under reduced pressure to give a yellow solid. The solid was purified by silica gel flash chromatography (0-30% MeOH in DCM+0.5% NH$_4$OH) to give the title compound (3.60 g, 82% yield) as a yellow solid.

LC-MS (Method 10-70): Rt 2.72 min; m/z 903.8 [M+H]$^+$.

Example 10

Preparation of Biphenyl-2-ylcarbamic Acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl Ester Ditrifluoroacetic Acid Salt To a stirred solution of biphenyl-2-ylcarbamic acid 1-(2-{[4-(4-{[(R)-2-(tert-butyldimethylsilanyloxy)-2-(8-hydroxy-2-oxo-1,2-dihydroquinolin-5-yl)ethylamino]methyl}phenylcarbamoyl)butyl]methylcarbamoyl}ethyl)piperidin-4-yl ester (3.60 g, 3.98 mmol) in a 9:1 mixture of DCM:DMF (32.9 mL) was added triethylamine trihydrofluoride (1.95 mL, 12.0 mmol). The resulting mixture was stirred at room temperature overnight and then concentrated under reduced pressure. The residue was purified by HPLC (Method 10-70) to give the title compound (1.90 g, 46% yield) as a white solid.

LC-MS (Method 10-70): Rt 2.12 min; m/z 789.6 [M+H]$^+$.

Example 11

Preparation of Biphenyl-2-ylcarbamic Acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl Ester Dihydrofluoric Acid Salt To a stirred solution of biphenyl-2-ylcarbamic acid 1-(2-{[4-(4-{[(R)-2-(tert-butyldimethylsilanyloxy)-2-(8-hydroxy-2-oxo-1,2-dihydroquinolin-5-yl)ethylamino]methyl}phenylcarbamoyl)butyl]methylcarbamoyl}ethyl)piperidin-4-yl ester (3.87 g, 4.28 mmol) in a mixture of DCM (20 mL) and DMF (2.5 mL) was added triethylamine trihydrofluoride (2.1 mL, 13 mmol). The resulting mixture was stirred at room temperature overnight. DCM (68 mL) was added to the reaction mixture and then, with stirring, EtOAc (68 mL) was added dropwise. A light colored precipitate formed resulting in a slurry. The slurry mixture was filtered through a medium porosity fritted glass filter and the filter cake was rinsed with EtOAc (2×10 mL) and then pressed dry on a nitrogen press to give the title compound (3.73 g, 99% yield).

Example 12

Preparation of Biphenyl-2-ylcarbamic Acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl Ester A solution of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl ester dihydrofluoric acid salt (15.2 g, 16.7 mmol) in a DCM solution containing 10% 0.5 M ammonium hydroxide in MeOH (150 mL total solution) was loaded onto silica gel (80 g) in a coarse fritted glass funnel which had been previously wetted with a DCM solution containing 10% 0.5 M ammonium hydroxide in MeOH (200 mL). The silica gel was rinsed with a DCM solution containing 20% 0.5 M ammonium hydroxide in MeOH (1×1000 mL); and then with a DCM solution containing 25% 0.5 M ammonium hydroxide in MeOH (1×1000 mL). The filtrate was concentrated under reduced pressure to give a yellow glassy solid (13.6 g). This material was dissolved in DCM (600 mL) and the resulting solution was filtered through a fritted glass filter and the filter was washed with DCM (3×150 mL). The filtrate was concentrated under reduced pressure and the residue was warmed to 50° C. using an oil bath and held under high vacuum overnight to provide the title compound (12.7 g) (contained about 6 wt. % of DCM).

Example 13

Preparation of a Crystalline Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl Ester Oxalate Hydrate Salt (Form 2)

To a stirred solution of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)-butyl]methylcarbamoyl}ethyl)piperidin-4-yl ester (0.50 g, 0.63 mmol) in THF (5 mL, 60 mmol) was added dropwise a solution of oxalic acid dihydrate (80 mg, 0.63 mmol) in MeOH (2 mL, 50 mmol). An off-white precipitate formed immediately and over a period of 5 min, the solid agglomerated to form a sticky ball. The reaction mixture was then heated at 60° C. for 2 h at which time the mixture had formed an off-white thick slurry of very fine particles. This mixture was cooled slowly to room temperature and then stirred for about 72 h. An attempt was made to filter the mixture but most of the precipitate when through the filter. The filtrate was then concentrated under reduced pressure to form a residue.

Approximately one-fourth of the residue was removed and dissolved in a hot solution of 10% (v/v) water in MeOH. This solution was cooled to room temperature but no precipitate formed. The solution was then allowed to stand and evaporate slowly at room temperature over a period of 4 days which produced particles showing some birefringence. Stirring was continued with occasional sonication over a period of 5 days to form a white slurry of material showing better birefringence. This material was collected by filtration and dried under high vacuum at room temperature for 2 h to give the title compound. A PXRD pattern showed this material to be crystalline or semi-crystalline.

Example 14

Preparation of a Crystalline Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl Ester Oxalate Hydrate Salt (Form 2)

To a stirred solution of biphenyl-2-ylcarbamic acid 1-(2-{[4-(4-{[(R)-2-hydroxy-2-(8-hydroxy-2-oxo-1,2-dihydro-quinolin-5-yl)ethylamino]methyl}phenylcarbamoyl)butyl]-methylcarbamoyl}ethyl)piperidin-4-yl ester (0.65 g, 0.824 mmol) in MeOH (12.4 mL) was added dropwise a solution of oxalic acid dihydrate (104 mg, 0.824 mmol) in water (0.6 mL). A slightly sticky precipitate formed immediately and seed crystals from Example 13 were added. The resulting slurry was stirred at room temperature for about 72 hours and then sonicated for 5 min. The slurry was then stirred at 30° C. overnight. The slurry was then cooled to 0° C., stirred for 30 min. and filtered to collect the precipitate. The filter cake was air dried for 1 h and then dried under high vacuum for 2 h at room temperature to give the title compound (705 mg, 96% yield, >99% purity).

Example 15

Exposure of Form 2 to High Relative Humidity

Biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester oxalate hydrate (approx. 100 mg; from Example 14) was spread on filter paper placed in a petri dish. The petri dish was placed in a dessicator on a porous plate above a saturated aqueous potassium chloride solution (100 mL) and the dessicator was tightly sealed. The relative humidity inside the chamber remained at approximately 84% RH as measured by a hygrometer. After three days, the solid was removed from the dessicator. The PXRD, DSC, TGA and DMS plots for this material are shown in FIGS. 4, 5, 6 and 7, respectively.

Example 16

Preparation of a Crystalline Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl Ester Oxalate Hydrate Salt (Form 2)

To a stirred solution of biphenyl-2-ylcarbamic acid 1-(2-{[4-(4-{[(R)-2-hydroxy-2-(8-hydroxy-2-oxo-1,2-dihydro-quinolin-5-yl)ethylamino]methyl}phenylcarbamoyl)-butyl]methylcarbamoyl}ethyl)piperidin-4-yl ester (1.0 g, 1.27 mmol) in MeOH (19 mL) was added dropwise a solution of oxalic acid dihydrate (160 mg, 1.269 mmol) in water (1.0 mL). A sticky yellowish precipitate formed immediately. The reaction mixture was heated at 40° C. overnight and then sonicated for 5 min. The reaction mixture was then heated at 40° C. for 18 h, cooled to 0° C., the precipitate was collected by filtration. The precipitate was dried to give the title compound (1.05 g, 93% yield, >99% purity).

Example 17

Exposure of Form 2 to High Relative Humidity

A supersaturated aqueous solution of potassium chloride was prepared in the bottom of a desiccator (solid KCl remained after extensive swirling). Biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}ethyl)piperidin-4-yl ester oxalate hydrate (500 mg, 0.569 mmol; from Example 16) was spread in a weighing paper and the weighing paper was placed on a porous plastic plate atop the KCl solution in the dessicator and the desiccator was closed. The relative humidity inside the dessicator was maintained at 84% RH due to the equilibrium vapor pressure of KCl solution. PXRD patterns were obtained on portions of the oxalate salt after 3, 5, and 10 days. The PXRD patterns showed that the crystallinity of the oxalate salt improved for up to 5 days. The change in crystallinity was negligible between 5 and 10 days.

Example 18

Preparation of a Crystalline Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl Ester Oxalate Hydrate Salt (Form 2)

To a stirred solution of biphenyl-2-ylcarbamic acid 1-(2-{[4-(4-{[(R)-2-hydroxy-2-(8-hydroxy-2-oxo-1,2-dihydro-quinolin-5-yl)ethylamino]methyl}phenylcarbamoyl)-butyl]methylcarbamoyl}ethyl)piperidin-4-yl ester (11.0 g, 13.9 mmol) in MeOH (400 mL) was added dropwise a solution of oxalic acid dihydrate (1.758 g, 13.9 mmol) in water (22 mL). A sticky precipitate formed immediately. The reaction mixture was stirred at room temperature overnight and then sonicated for 5 min. The reaction mixture was then stirred at room temperature for 48 h and then heated at 40° C. for 8 h. The reaction mixture was allowed to slowly cool to ambient temperature and then it was heated at 30° C. for about 72 h. The precipitate was collected by filtration, washed with MeOH (1×50 mL), and dried under high vacuum overnight to give the title compound (11.6 g, 94% yield, >99% purity).

Example 19

Preparation of a Crystalline Biphenyl-2-ylcarbamic Acid 1-(2-{[4-(4-{[(R)-2-Hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl Ester Oxalate Isopropanol Solvate Salt (Form 1)

Crystalline biphenyl-2-ylcarbamic Acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl)piperidin-4-yl ester oxalate hydrate (approx. 40 mg) was suspended in a solution of 5% (v/v) water in isopropanol (4 mL) and the resulting slurry was stirred at 200 rpm at room temperature. After three days, the slurry was filtered by suction filtration and the solid was dried in air to give the title compound (36 mg).

Figure 1:
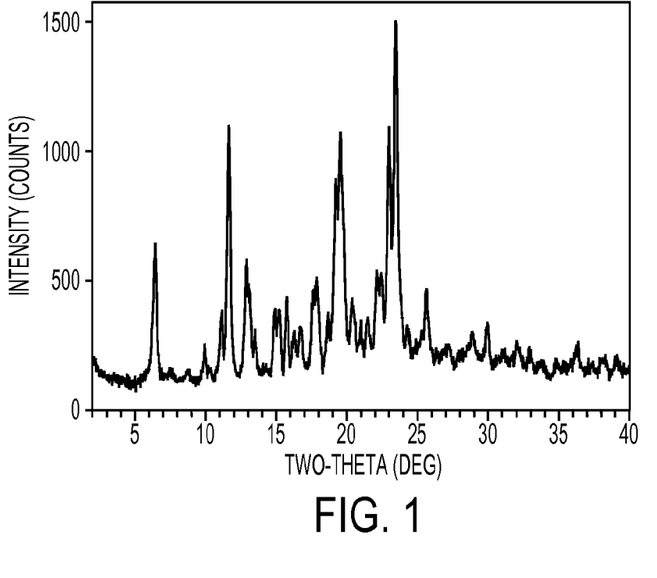
FIG. 1 shows a powder x-ray diffraction (PXRD) pattern for a crystalline oxalate isopropanol solvate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl)piperidin-4-yl ester (Form 1).
Figure 2:
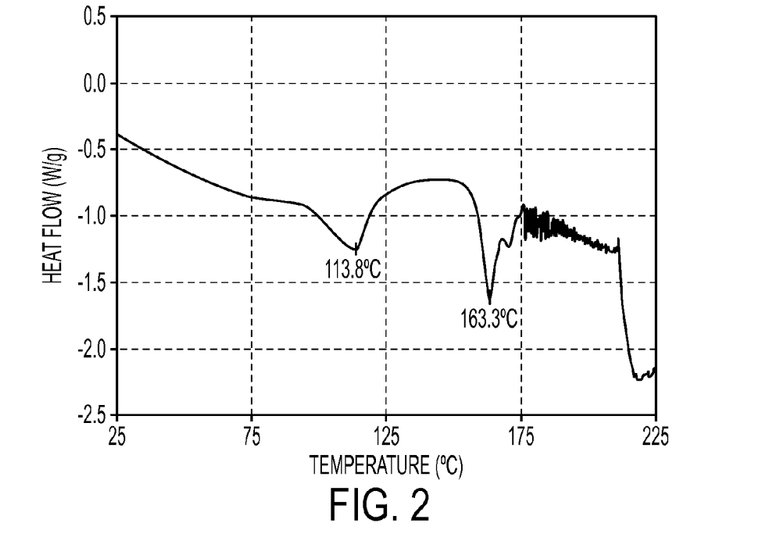
FIG. 2 shows a differential scanning calorimetry (DSC) trace for a crystalline oxalate isopropanol solvate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl) piperidin-4-yl ester (Form 1).
Figure 3:
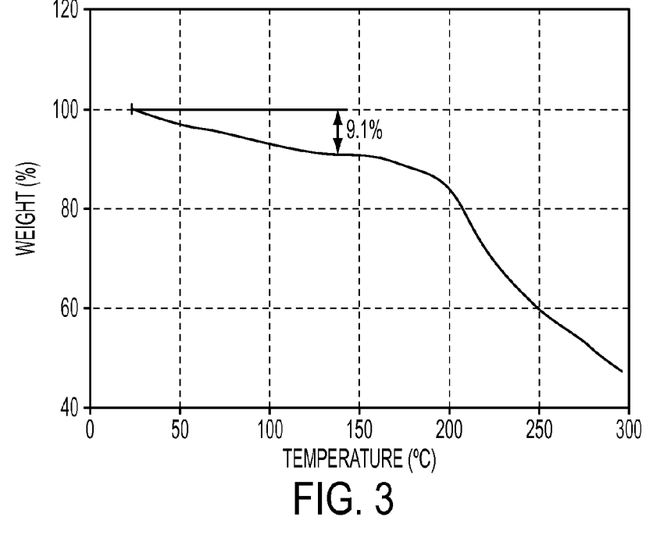
FIG. 3 shows a thermal gravimetric analysis (TGA) trace for a crystalline oxalate isopropanol solvate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl) piperidin-4-yl ester (Form 1).

The PXRD, DSC and TGA spectra for this material are shown in FIGS. 1, 2 and 3, respectively.

Example 20

Powder X-Ray Diffraction

Powder X-ray diffraction analysis was performed using the Rigaku MiniFlex X-ray diffractometer. The X-ray source was Cu-Kα radiation (λ=1.54051 Å) with output voltage of 20 kV and current of 15 mA. The instrument was operated in Bragg-Brentano geometry with incident, divergence, and scattering slits set to maximize the intensity at the sample. For measurement, a small amount of powder (5-25 mg) was gently pressed onto the single crystal silicon sample holder to form a smooth surface and subjected to X-ray exposure. The samples were scanned in 2θ-θ mode from 2° to 40° in 2θ with a step size of 0.03° and a scan speed of 2.0° per minute. The data acquisition was controlled by Rigaku Standard easurement software (Version 1.2.0.0) and analyzed by Jade software (version 7.5.1).

Figure 4:
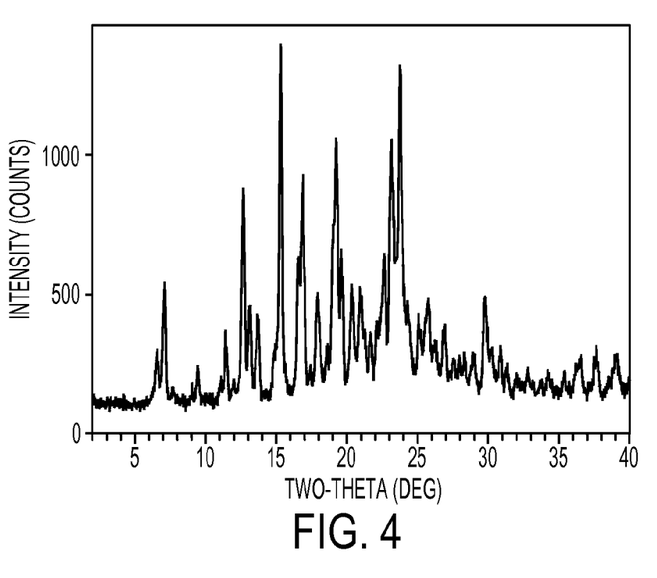
FIG. 4 shows a powder x-ray diffraction (PXRD) pattern for a crystalline oxalate hydrate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl) piperidin-4-yl ester (Form 2).

Representative raw unprocessed PXRD patterns for Form 1 and Form 2 are shown in FIG. 1 and FIG. 4, respectively. Observed PXRD two-theta peak positions and d-spacings for Form 1 and Form 2 are shown in Tables 1 and 2, respectively (only peaks having a relative peak height (H %) of about 20% or greater are listed).

TABLE 1

PXRD Data for Form 1

| Peak No. | 2-Theta | d (Å) | Height[1] | H %[2] |
|---|---|---|---|---|
| 1 | 6.44 | 13.72 | 519 | 43.8 |
| 2 | 11.15 | 7.93 | 253 | 21.3 |
| 3 | 11.66 | 7.58 | 959 | 80.9 |
| 4 | 12.92 | 6.85 | 434 | 36.7 |
| 5 | 15.75 | 5.62 | 230 | 19.4 |
| 6 | 17.84 | 4.97 | 326 | 27.5 |
| 7 | 19.19 | 4.62 | 653 | 55.1 |
| 8 | 19.55 | 4.54 | 786 | 66.3 |
| 9 | 23.00 | 3.86 | 738 | 62.3 |
| 10 | 23.45 | 3.79 | 1185 | 100 |
| 11 | 25.61 | 3.48 | 263 | 22.2 |

[1]Peak height from base line.
[2]Percent peak height compared to highest peak.

TABLE 2

PXRD Data for Form 2

| Peak No. | 2-Theta | d (Å) | Height[1] | H %[2] |
|---|---|---|---|---|
| 1 | 7.10 | 12.44 | 420 | 33.6 |
| 2 | 12.68 | 6.98 | 704 | 56.4 |
| 3 | 13.15 | 6.73 | 303 | 24.2 |
| 4 | 13.68 | 6.47 | 244 | 19.6 |
| 5 | 15.32 | 5.78 | 1249 | 100 |
| 6 | 16.58 | 5.34 | 465 | 37.2 |
| 7 | 16.90 | 5.24 | 750 | 60.1 |
| 8 | 17.93 | 4.94 | 305 | 24.4 |
| 9 | 19.25 | 4.61 | 839 | 67.2 |
| 10 | 19.61 | 4.52 | 422 | 33.8 |
| 11 | 20.34 | 4.36 | 265 | 21.2 |
| 12 | 20.93 | 4.24 | 301 | 24.1 |
| 13 | 22.64 | 3.92 | 285 | 22.8 |
| 14 | 23.15 | 3.84 | 657 | 52.6 |
| 15 | 23.73 | 3.75 | 1007 | 80.7 |
| 16 | 25.76 | 3.46 | 257 | 20.6 |
| 17 | 29.78 | 3.00 | 309 | 24.7 |

[1]Peak height from base line.
[2]Percent peak height compared to highest peak.

Example 21

Differential Scanning Calorimetry

Figure 5:
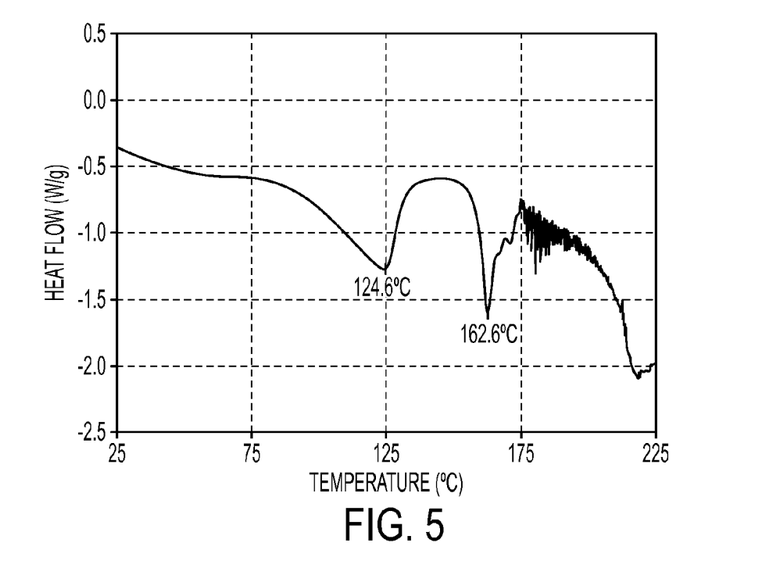
FIG. 5 shows a differential scanning calorimetry (DSC) trace for a crystalline oxalate hydrate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl) piperidin-4-yl ester (Form 2).

Differential scanning calorimetry (DSC) was performed using a TA Instruments Model Q-100 module with a Thermal Analyst controller. Data were collected and analyzed using TA Instruments Thermal Solutions software. A sample of about 2 mg was accurately weighed into an aluminum pan with lid. The sample was evaluated using a linear heating ramp of 10° C./min from ambient temperature to approximately 300° C. The DSC cell was purged with dry nitrogen during use. Representative DSC traces for Form 1 and Form 2 are shown in FIG. 2 and FIG. 5, respectively.

The DSC traces demonstrate that Form 1 and Form 2 have excellent thermal stability with melting points in the range of about 162° C. to 164° C.

Example 22

Thermogravimetric Analysis

Figure 6:
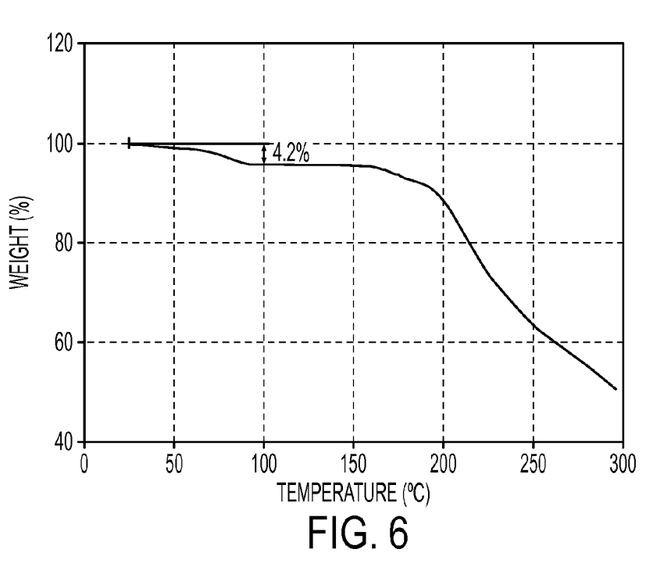
FIG. 6 shows a thermal gravimetric analysis (TGA) trace for a crystalline oxalate hydrate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl) piperidin-4-yl ester (Form 2).

Thermogravimetric analysis (TGA) was performed using a TA Instruments Model Q-500 module equipped with high resolution capability. Data were collected and analyzed using TA Instruments Thermal Solutions software. A sample weighing about 10 mg was placed onto a platinum pan and scanned with a high resolution-heating rate from ambient temperature to 300° C. The balance and furnace chambers were purged with nitrogen flows during use. Representative TGA traces for Form 1 and Form 2 are shown in FIG. 3 and FIG. 6, respectively.

Example 23

Dynamic Moisture Sorption Assessment

A dynamic moisture sorption (DMS) assessment (also known as a moisture sorption-desorption profile) was performed for a sample of Form 2 using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 5% relative humidity (RH), 5% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points. A representative DMS trace for Form 2 is shown in FIG. 7.

Figure 7:
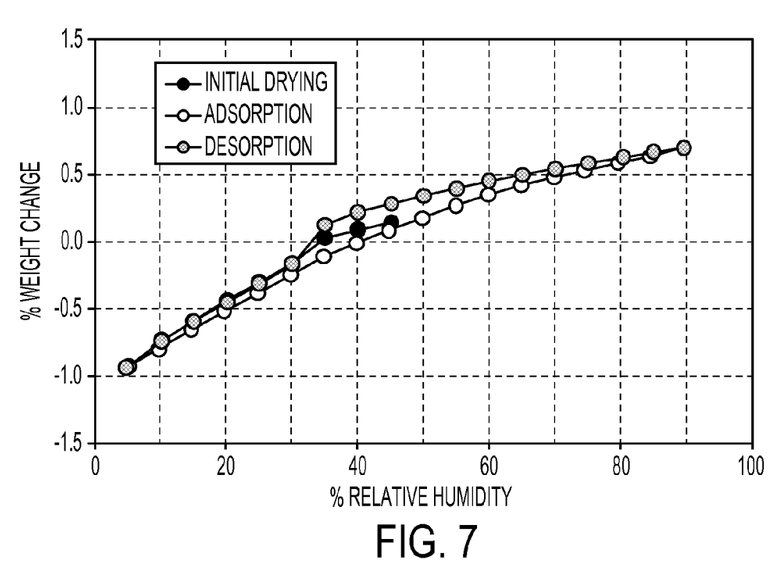
FIG. 7 shows a dynamic moisture sorption (DMS) trace for a crystalline oxalate hydrate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]-methylcarbamoyl}ethyl) piperidin-4-yl ester (Form 2).

The DMS trace of FIG. 7 demonstrates that Form 2 had an insignificant weight gain of about 1.6 weight % in the humidity range of 5% RH to 90% RH. The reversible moisture sorption/desorption profile demonstrates that Form 2 possesses an acceptable hygroscopicity and is not deliquescent. The PXRD profiles of the salt were similar before and after the DMS experiment suggesting that no change in physical form occurred during the moisture sorption and moisture desorption processes.

Biological Assays and Preparations

Example A

Cell Culture and Membrane Preparation from Cells Expressing Human $M_1$, $M_2$, $M_3$ and $M_4$ Muscarinic Receptors CHO cell lines stably expressing cloned human $hM_1$, $hM_2$, $hM_3$ and $hM_4$ muscarinic receptor subtypes, respectively, were grown to near confluency in Hams F-12 media supplemented with 10% FBS and 250 μg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80 EC or membranes were prepared immediately for use.

For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with re-suspension buffer and homogenized again with the Polytron tissue disrupter.

The protein concentration of the membrane suspension was determined by the method described in Lowry et al., 1951, *Journal of Biochemistry*, 193, 265. All membranes were stored frozen in aliquots at −80° C. or used immediately.

Aliquots of prepared $hM_5$ receptor membranes were purchased from PerkinElmer, Inc. (Wellesley, Mass.) and were stored at −80° C. until use.

Example B

Radioligand Binding Assay for Muscarinic Receptors

Radioligand binding assays for cloned muscarinic receptors were performed in 96-well microtiter plates in a total assay volume of 100 μL. CHO cell membranes stably expressing either the $hM_1$, $hM_2$, $hM_3$, $hM_4$ or $hM_5$ muscarinic subtype were diluted in assay buffer to the following specific target protein concentrations (μg/well): 10 μg for $hM_1$, 10-15 μg for $hM_2$, 10-20 μg for $hM_3$, 10-20 μg for $hM_4$, and 10-12 μg for $hM_5$ to get similar signals (cpm). The membranes were briefly homogenized using a Polytron tissue disruptor (10 seconds) prior to assay plate addition.

Saturation binding studies for determining $K_D$ values of the radioligand were performed using L-[N-methyl-$^3$H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM.

Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 pM to 100 μM. The order of addition and volumes added to the assay plates were as follows: 25 μL radioligand, 25 μL diluted test compound, and 50 μL membranes. Assay plates were incubated for 6 hours at 37° C. Binding reactions were terminated by rapid filtration over GF/B glass fiber filter plates (PerkinElmer, Inc.) pre-treated in 1% BSA. Filter plates were rinsed three times with wash buffer (10 mM HEPES) to remove unbound radioactivity. The plates were then air-dried and 50 μL Microscint-20 liquid scintillation fluid (PerkinElmer, Inc.) were added to each well. The plates were then counted in a PerkinElmer Topcount liquid scintillation counter (PerkinElmer, Inc.).

Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W H. (1973) *Biochemical Pharmacology*, 22(23):3099-108). $K_i$ values were converted to $pK_i$ values to determine the geometric mean and 95% confidence intervals. These summary statistics were then converted back to $K_i$ values for data reporting.

In this assay, a lower $K_i$ value means the test compound has a higher binding affinity for the receptor. Biphenyl-2-ylcarbamic acid 1-(2-{[4-(4-{[(R)-2-hydroxy-2-(8-hydroxy-2-oxo-1,2-dihydroquinolin-5-yl)ethylamino]-methyl}phenylcarbamoyl)-butyl]methylcarbamoyl}ethyl) piperidin-4-yl ester ditrifluoroacetic acid salt had a $K_i$ value at $hM_3$ of 0.1 nM (data rounded to nearest 0.1 nM) in this assay.

Example C

Cell Culture and Membrane Preparation from Cells Expressing Human $β_1$, $β_2$ or $β_3$ Adrenergic Receptors Human embryonic kidney (HEK-293) cell lines stably expressing cloned human $β_1$ and $β_2$ adrenergic receptors or Chinese hamster ovarian (CHO) cell lines stably expressing cloned human $\beta_3$ adrenergic receptors were grown to near confluency in DMEM or Hams F-12 media with 10% FBS in the presence of 500 µg/mL Geneticin. The cell monolayer was lifted with 2 mM EDTA in PBS. Cells were pelleted by centrifugation at 1,000 rpm, and cell pellets were either stored frozen at −80° C. or membranes were prepared immediately for use.

For preparation of $\beta_1$ and $\beta_2$ receptor expressing membranes, cell pellets were re-suspended in lysis buffer (10 mM HEPES/HCl, 10 mM EDTA, pH 7.4 at 4° C.) and homogenized using a tight-fitting Dounce glass homogenizer (30 strokes) on ice.

For the more protease-sensitive $\beta_3$ receptor expressing membranes, cell pellets were homogenated in lysis buffer (10 mM Tris/HCl, pH 7.4) supplemented with one tablet of "Complete Protease Inhibitor Cocktail Tablets with 2 mM EDTA" per 50 mL buffer (Roche Molecular Biochemicals, Indianapolis, Ind.). The homogenate was centrifuged at 20,000×g, and the resulting pellet was washed once with lysis buffer by re-suspension and centrifugation as described herein. The final pellet was then re-suspended in ice-cold binding assay buffer (75 mM Tris/HCl pH 7.4, 12.5 mM $MgCl_2$, 1 mM EDTA).

The protein concentration of the membrane suspension was determined by the methods described in Lowry et al., 1951, *Journal of Biological Chemistry*, 193, 265; and Bradford, *Analytical Biochemistry*, 1976, 72, 248-54. All membranes were stored frozen in aliquots at −80° C. or used immediately.

Example D

Assay for Determining Adrenergic Receptor Agonist Potency cAMP assays were performed in a radioimmunoassay format using the Flashplate Adenylyl Cyclase Activation Assay System with [$^{125}$I]-cAMP (NEN SMP004, PerkinElmer Life Sciences Inc., Boston, Mass.), according to the manufacturers instructions. For this assay, HEK-293 cell lines stably expressing cloned human $\beta_1$ or $\beta_2$ receptors were grown to near confluency in DMEM supplemented with 10% FBS and Geneticin (500 µg/mL); or CHO-K1 cell lines stably expressing cloned human $\beta_3$ adrenergic receptors were grown to near confluency in Hams F-12 media supplemented with 10% FBS and Geneticin (250 µg/mL). Cells were rinsed with PBS and detached in dPBS (Dulbecco's Phosphate Buffered Saline, without $CaCl_2$ and $MgCl_2$) containing 2 mM EDTA or Trypsin-EDTA solution (0.05% trypsin/0.53 mM EDTA). After counting cells in Coulter cell counter, cells were pelleted by centrifugation at 1,000 rpm and re-suspended in stimulation buffer containing IBMX (PerkinElmer Kit) pre-warmed to room temperature to a concentration of $1.6 \times 10^6$ to $2.8 \times 10^6$ cells/mL. About 40,000 to 80,000 cells per well were used in this assay. Test compounds (10 mM in DMSO) were diluted into PBS containing 0.1% BSA in Beckman Biomek-2000 and tested at 11 different concentrations ranging from 100 µM to 1 pM. Reactions were incubated for 10 min at 37° C. and stopped by adding 100 µL of cold detection buffer containing [$^{125}$I]-cAMP (NEN SMP004, PerkinElmer Life Sciences, Boston, Mass.). The amount of cAMP produced (pmol/well) was calculated based on the counts observed for the samples and cAMP standards as described in the manufacturer's user manual.

Data were analyzed by nonlinear regression analysis with the GraphPad Prism Software package (GraphPad Software, Inc., San Diego, Calif.) with the sigmoidal equation. The Cheng-Prusoff equation (Cheng Y, and Prusoff W H., *Biochemical Pharmacology*, 1973, 22, 23, 3099-108) was used to calculate the $EC_{50}$ values.

In this assay, a lower $EC_{50}$ value means the test compound has a higher functional activity at the receptor tested. Biphenyl-2-ylcarbamic acid 1-(2-{[4-(4-{[(R)-2-hydroxy-2-(8-hydroxy-2-oxo-1,2-dihydroquinolin-5-yl)ethylamino]-methyl}phenylcarbamoyl)-butyl]methylcarbamoyl}ethyl) piperidin-4-yl ester ditrifluoroacetic acid salt had a $EC_{50}$ value at h$\beta_2$ of 1 nM (data rounded to nearest 1 nM) in this assay.

Example E

Einthoven Assay

This assay measures the ability of a test compound to provide bronchoprotection against methacholine (MCh)-induced bronchoconstriction in a rat.

Male Sprague-Dawley rats (Harlan, Indianapolis, Ind.), weighing between 200 g and 350 g, were used for all studies.

Test compound or vehicle (sterile deionized water) were dosed by inhalation (IH) over a 10 min period in a pie shaped inhalation chamber (R+S Molds, San Carlos, Calif.) using 5 mL of dosing solution. Rats were exposed to an aerosol, which was generated from an LC Star Nebulizer Set Model 22F51 (PARI Respiratory Equipment, Inc. Midlothian, Va.) driven by Bioblend (5% CO2/95% atmospheric air) at a pressure of 22 psi. Rats were dosed with 100 µg of test compound unless otherwise indicated.

At predetermined time points, rats were anesthetized with an intraperitoneal (IP) injection of 120 mg/kg inactin (thiobutabarbital). A supplemental dose (40 mg/kg, IP) was administered if the animal responded to physical stimuli (e.g. toe pinch). The surgical site was shaved and a 1-2 cm midline incision of the ventral aspect of the neck was made. The jugular vein was isolated and cannulated with a saline-filled polyethylene catheter (PE-50) to allow IV infusion of MCh. Trachea was dissected free and cannulated with a 14 G needle (#NE-014, Small Parts, Miami Lakes, Fla.). After placement of the tracheal cannula, each rat was ventilated using a respirator (Model 683, Harvard Apparatus, Inc., MA) set at a stroke volume of 1 mL/100 g body weight (but not exceeding 2.5 mL volume) and a rate of 90 strokes per minute. A T-connector was placed along the respirator expiratory tubing to allow for measurement of changes in ventilation pressure (VP) using a Biopac transducer that was connected to a Biopac (TSD 137C) pre-amplifier. Body temperature was maintained at 37° C. using a heating pad.

Changes in VP were recorded using the Acknowledge Data Collection Software (Santa Barbara, Calif.). Baseline values were collected for at least 2.5 min. Rats were then challenged with non-cumulative intravenous (IV) infusions of 40 and 80 µg/kg MCh. MCh was infused intravenously for 2.5 minutes from a syringe pump (sp210iw, World Precision Instruments, Inc., Sarasota, Fla.) at a rate of 2 mL/kg/min, with a 2 minute interval between the two doses of MCh. Changes in ventilation pressure (cm $H_2O$) in treated animals are expressed as % inhibition of MCh response relative to control animals.

Other bronchoconstrictors, such as histamine and acetylcholine, can be used in place of MCh in this assay. Additonally, guinea pigs can be used instead of rats.

In this assay, a higher % inhibition of the MCh response indicates that the test compound provided a greater bronchoprotective effect Inhibition greater than or equal to 30 percent at 24 h is indicative of a long duration of action. Biphenyl-2- ylcarbamic acid 1-(2-{[4-(4-{[(R)-2-hydroxy-2-(8-hydroxy-2-oxo-1,2-dihydroquinolin-5-yl)ethylamino]-methyl}phenylcarbamoyl)butyl]methylcarbamoyl}ethyl) piperidin-4-yl ester ditrifluoroacetic acid salt provided at least about 40 percent inhibition at 24 h in this assay.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statutes and regulations, all publications, patents and patent applications cited herein are hereby incorporated by reference in their entirety to the same extent as if each document had been individually incorporated by reference herein.

What is claimed is:

1. A crystalline oxalate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}-phenylcarbamoyl)butyl]methylcarbamoyl}ethyl)piperidin-4-yl ester; wherein the crystalline oxalate salt is selected from:
   (a) an isopropanol solvate characterized by a powder x-ray diffraction pattern comprising diffraction peaks at 2θ values of 11.66±0.20, 15.75±0.20, 19.55±0.20, 23.00±0.20 and 23.45±0.20; and
   (b) a hydrate characterized by a powder x-ray diffraction pattern comprising diffraction peaks at 2θ values of 15.32±0.20, 16.90±0.20, 19.25±0.20 and 23.73±0.20.

2. A crystalline oxalate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester, wherein the crystalline oxalate salt is an isopropanol solvate characterized by a powder x-ray diffraction pattern comprising diffraction peaks at 2θ values of 11.66±0.20, 15.75±0.20, 19.55±0.20, 23.00±0.20 and 23.45±0.20.

3. The crystalline oxalate salt of claim 2, wherein the crystalline oxalate salt is characterized by a powder x-ray diffraction pattern in which the peak positions are substantially in accordance with the peak positions of the pattern shown in FIG. 1.

4. The crystalline oxalate salt of claim 2, wherein the crystalline oxalate salt is characterized by a melting point in the range of about 162° C. to about 164° C.

5. The crystalline oxalate salt of claim 2, wherein the crystalline oxalate salt is characterized by a differential scanning calorimetry trace substantially in accordance with that shown in FIG. 2.

6. A crystalline oxalate salt of biphenyl-2-ylcarbamic acid 1-(2-{[4-(4-{[(R)-2-hydroxy-2-(8-hydroxy-2-oxo-1,2-dihydroquinolin-5-yl)ethylamino]methyl}phenylcarbamoyl)butyl]methylcarbamoyl}-ethyl)piperidin-4-yl ester, wherein the crystalline oxalate salt is a hydrate characterized by a powder x-ray diffraction pattern comprising diffraction peaks at 2θ values of 15.32±0.20, 16.90±0.20, 19.25±0.20 and 23.73±0.20.

7. The crystalline oxalate salt of claim 6, wherein the crystalline oxalate salt is characterized by a powder x-ray diffraction pattern in which the peak positions are substantially in accordance with the peak positions of the pattern shown in FIG. 4.

8. The crystalline oxalate salt of claim 6, wherein the crystalline oxalate salt is characterized by a melting point in the range of about 162° C. to about 164° C.

9. The crystalline oxalate salt of claim 6, wherein the crystalline oxalate salt is characterized by a differential scanning calorimetry trace substantially in accordance with that shown in FIG. 5.

10. A pharmaceutical composition comprising:
   (a) a crystalline oxalate salt of claim 1; and
   (b) a pharmaceutically-acceptable carrier.

11. A pharmaceutical composition comprising:
   (a) crystalline oxalate salt of claim 1;
   (b) a steroidal anti-inflammatory agent or a pharmaceutically acceptable salt or solvate thereof; and
   (c) a pharmaceutically-acceptable carrier.

12. A method of treating a pulmonary disorder, the method comprising administering to a patient a crystalline oxalate salt of claim 1.

13. The method of claim 12, wherein the pulmonary disorder is chronic obstructive pulmonary disease or asthma.

14. A method of treating a pulmonary disorder, the method comprising administering to a patient (a) a crystalline oxalate salt of claim 1; and (b) a steroidal anti-inflammatory agent or a pharmaceutically acceptable salt or solvate thereof.

15. The method of claim 14, wherein the pulmonary disorder is chronic obstructive pulmonary disease or asthma.

16. A method of producing bronchodilation in a mammal, the method comprising administering a crystalline oxalate salt of claim 1 to the mammal by inhalation.

17. A pharmaceutical composition comprising:
   (a) a crystalline oxalate salt of claim 2; and
   (b) a pharmaceutically-acceptable carrier.

18. A pharmaceutical composition comprising:
   (a) a crystalline oxalate salt of claim 2;
   (b) a steroidal anti-inflammatory agent or a pharmaceutically acceptable salt or solvate thereof; and
   (c) a pharmaceutically-acceptable carrier.

19. A method of treating a pulmonary disorder, the method comprising administering to a patient a crystalline oxalate salt of claim 2.

20. The method of claim 19, wherein the pulmonary disorder is chronic obstructive pulmonary disease.

21. The method of claim 19, wherein the pulmonary disorder is asthma.

22. A method of treating a pulmonary disorder, the method comprising administering to a patient (a) a crystalline oxalate salt of claim 2; and (b) a steroidal anti-inflammatory agent or a pharmaceutically acceptable salt or solvate thereof.

23. The method of claim 22, wherein the pulmonary disorder is chronic obstructive pulmonary disease.

24. The method of claim 22, wherein the pulmonary disorder is asthma.

25. A method of producing bronchodilation in a mammal, the method comprising administering a crystalline oxalate salt of claim 2 to the mammal by inhalation.

26. A pharmaceutical composition comprising:
   (a) a crystalline oxalate salt of claim 6; and
   (b) a pharmaceutically-acceptable carrier.

27. A pharmaceutical composition comprising:
   (a) a crystalline oxalate salt of claim 6;
   (b) a steroidal anti-inflammatory agent or a pharmaceutically acceptable salt or solvate thereof; and
   (c) a pharmaceutically-acceptable carrier.

28. A method of treating a pulmonary disorder, the method comprising administering to a patient a crystalline oxalate salt of claim 6.

29. The method of claim 28, wherein the pulmonary disorder is chronic obstructive pulmonary disease.

30. The method of claim 28, wherein the pulmonary disorder is asthma.

31. A method of treating a pulmonary disorder, the method comprising administering to a patient (a) a crystalline oxalate salt of claim 6; and (b) a steroidal anti-inflammatory agent or a pharmaceutically acceptable salt or solvate thereof.

32. The method of claim 31, wherein the pulmonary disorder is chronic obstructive pulmonary disease.

33. The method of claim 31, wherein the pulmonary disorder is asthma.

34. A method of producing bronchodilation in a mammal, the method comprising administering a crystalline oxalate salt of claim 6 to the mammal by inhalation.

* * * * *